US005686308A

United States Patent [19]
Li et al.

[11] Patent Number: 5,686,308
[45] Date of Patent: Nov. 11, 1997

[54] REAGENT AND METHOD FOR DIFFERENTIAL DETERMINATION OF LEUKOCYTES IN BLOOD

[75] Inventors: Yi Li; Carole Young, both of Miami, Fla.; Timothy J. Fischer, Raleigh, N.C.; James H. Carter, Plantation, Fla.

[73] Assignee: Coulter Corporation, Miami, Fla.

[21] Appl. No.: 488,630

[22] Filed: Jun. 8, 1995

[51] Int. Cl.⁶ .................. G01N 33/48; G01N 31/00
[52] U.S. Cl. ............... 436/63; 436/8; 436/10; 436/17; 436/18
[58] Field of Search ................ 436/8, 10, 17, 436/18, 63

[56] References Cited

U.S. PATENT DOCUMENTS

| | | | |
|---|---|---|---|
| 3,741,875 | 6/1973 | Ansley et al. | 436/63 X |
| 4,185,964 | 1/1980 | Lancaster | 436/17 |
| 4,286,963 | 9/1981 | Ledis et al. | 436/17 |
| 4,330,341 | 5/1982 | May et al. | 106/308 N |
| 4,485,175 | 11/1984 | Ledis et al. | 436/63 |
| 4,525,296 | 6/1985 | Quinlan | 252/391 |
| 4,528,274 | 7/1985 | Carter et al. | 436/17 X |
| 4,968,629 | 11/1990 | Lapicola | 436/17 X |
| 5,116,539 | 5/1992 | Hamaguchi et al. | 252/408.1 |
| 5,125,737 | 6/1992 | Rodriguez et al. | 365/39 |
| 5,155,044 | 10/1992 | Ledis et al. | 436/17 |
| 5,196,346 | 3/1993 | Lefevre et al. | 436/63 |
| 5,198,485 | 3/1993 | King et al. | 524/243 |
| 5,242,832 | 9/1993 | Sakata | 436/17 |
| 5,250,437 | 10/1993 | Toda et al. | 436/10 |
| 5,389,549 | 2/1995 | Hamaguchi et al. | 436/10 |

FOREIGN PATENT DOCUMENTS

| | | |
|---|---|---|
| 0325710 | 8/1989 | European Pat. Off. . |
| 47-20478 | 9/1972 | Japan . |
| 62-112695 | 5/1987 | Japan . |

OTHER PUBLICATIONS

J. Witaszczyk *Tech. Wlok*, 1978, 27, 238–241.
N. Sawada *Igaku to Seibutsugaku* 1980, 100, 67–72.
Z. Byczkowska *Bromatol. Chem. Toksylcol.* 1983, 16, 49–52.
C.G. van Ginkel et al. *Biodegradation* 1993, 3, 435–443.

*Primary Examiner*—Arlen Soderquist
*Attorney, Agent, or Firm*—Mitchell E. Alter

[57] ABSTRACT

A lytic reagent composition is provided which selectively stromatolyses red blood cells in a blood sample. In addition, a lytic reagent system is provided which enable the differentiation of at least two subpopulations of leukocytes. A method for using the lytic reagent system is also provided. Still further, the lytic reagent system find use in the determination of the hemoglobin in the blood. The lytic reagent system utilizes an ethoxylated long chain compound based lysis reagent with an acid and a hypertonic, alkaline, stabilizing reagent. The system and analysis method maintains the cellular morphology of the leukocytes and can be used to analyze normal and abnormal blood samples, fresh and aged blood, human and non-human animal blood samples, as well as other fluid samples such as bone marrow.

35 Claims, 16 Drawing Sheets

REAGENT AND METHOD FOR DIFFERENTIAL DETERMINATION OF LEUKOCYTES IN BLOOD

FIELD OF THE INVENTION

The present invention relates to lytic and stabilizing reagents and a method to enable the determination of at least two populations of leukocytes in a single whole blood sample by means of suitable electronic instrumentation. In addition, the present invention relates to a reagent and a method useful for determining total hemoglobin in blood wherein the reagents are cyanide free.

BACKGROUND OF THE INVENTION

Analysis of leukocyte populations from whole blood samples is an integral and essential part of diagnostic procedures regarding a multiplicity of pathologies. The ability to analyze the major subpopulations of leukocytes in an automated manner is essential for a rapid diagnosis of a single blood sample and for the rapid processing of many samples at once.

Traditional diagnosis of blood samples involves the smearing of a blood sample on a microscope slide, followed by manual visual analysis of the individual slide. This approach is obviously extremely time consuming as well as being subjective to the interpretation of the individual analyzing the slide. These factors have led to the development of automated leukocyte analysis utilizing flow cytometry. An essential step in the use of automated leukocyte analysis using hematology instruments is the lysis of the red blood cells. Thus far, several lysis reagents have been developed for use in whole blood samples.

U.S. Pat. No. 4,286,963 (to Ledis et al.) describes a lytic reagent and a method for achieving rapid hemolysis of erythrocytes in whole blood and automated analysis of lymphoid and myeloid subpopulations of leukocytes and the quantitative determination of hemoglobin. The lytic reagent is composed of a mixture of at least one quaternary ammonium surfactant and an aryl substituted short chain alkanol in buffered aqueous medium (pH 3.5 to 5.0). However, this reagent is limited in its ability to differentiate the leukocytes into two (2) principal subpopulations: the lymphoid and myeloid fractions.

U.S. Pat. No. 4,485,175 (to Ledis et al.) describes a reagent system and method for performing differential determinations of leukocytes into three (3) subpopulations utilizing automated cell counting equipment. This reagent system contains a blood diluent and a lytic reagent, comprising a mixture of quaternary ammonium surfactants. However, this reagent system limited its application to effect differentiation of the leukocytes into three (3) subpopulations: lymphocytes, monocytes and granulocytes.

Quaternary ammonium surfactants are strongly hemolytic and the methods of both patents described above can cause lysis of the leukocytes. The differentiation, consequently, is based on the nuclear volumes of the leukocyte subpopulations. The application of these methods, alone or in combination with other means prohibits further refinement in the diagnostic process of various disease states based on the differences in the immunochemical response of the surface marker of the cell membrane.

U.S. Pat. No. 5,155,044 (to Ledis et al.) discloses a method and reagent system for the rapid isolation and analysis of leukocytes from a whole blood sample and enables automated differentiation into five (5) subpopulations utilizing an automated hematology analyzer. The reagent system is composed of an aqueous lytic reagent which comprises formic acid (or a formic acid/acetic acid mixture), or a mixture of formic acid and saponin, and an aqueous salt quench solution. However, the saponin used in this reagent system is a natural product. As a result of being a natural product, there is the potential of their being a finite source of saponin. In addition, the quality of the saponin can vary depending on its source.

In addition, acid lysing is known in the literature and this property has been utilized in automated hematology analyzers as discussed in U.S. Pat. No. 5,155,044, U.S. Pat. No. 5,196,346, and U.S. Pat. No. 5,389,549. However, lysis of the red blood cells using acid alone takes a long time and the red cell ghosts and debris are difficult to disrupt or dissolve to a size that does not interfere with the white cell differentials when the white cell counting is accomplished using DC and RF detection techniques.

Alternative lysis reagent systems have nonionic or anionic polyoxyethylene surfactants as discussed in U.S. Pat. No. 5,116,539, U.S. Pat. No. 5,389,549 and U.S. Pat. No. 5,196,346.

U.S. Pat. No. 5,196,346 (to Leferre et al.) describes an acid based lysis system which incorporates a polyoxyethylene ether surfactant. However, this reagent system was formulated for the limited analysis of the basophil population subsequent to lysis of all other leukocytes.

U.S. Pat. No. 5,116,539 (to Hamaguchi et al.) describes a reagent system designed for the lysis of red blood cells which contains a nonionic polyoxyethylene surfactant. However, this system permits only total leukocyte counting or eosinophil counting. The differentiation and determination of other leukocyte populations cannot be done with this lysis reagent system.

U.S. Pat. No. 5,384,549 (to Hamaguchi et al.) also describes a lysis reagent system which contains a nonionic polyoxyethylene surfactant. While the lysis reagent systems presented in this patent appears to maintain the integrity of the leukocyte population better than acid lysis techniques, it is still difficult to do a full analysis of the five major leukocyte subpopulations. Full analysis of leukocyte subpopulations requires differential lysis of the erythrocytes and leukocytes and three separate determinations for the identity of eosinophil, neutrophil and basophil populations in addition to the lymphocyte and monocyte populations. Additionally, this system requires a hypotonic lysing environment which is extremely shocking to the cells and makes preservation of the cells in a near native state difficult.

Previous lysis reagents utilizing polyoxyethylene surfactants exclusively use nonionic or anionic, preferably nonionic forms of a polyoxyethylene surfactant. These surfactants are limited in their use to either a single leukocyte cell population or when used for a multiple leukocyte subpopulation determination, the determination must be accomplished using a complex three-step flow cytometry analysis procedure. The nonionic polyoxyethylene surfactants are further limited in that they require a hypotonic environment to effectively lyse the red blood cells, which cause a traumatic osmotic shock to the cells which can be very damaging and can adversely affect the ability to analyze cells in their near native physiological state.

In addition, measuring the hemoglobin in a blood sample is another diagnostic tool when doing blood analysis. Historically, hemoglobin determinations have been performed by forming and measuring cyanide hemoglobin (Hb). However, the reagent waste from this method is of enormous environmental concern. Several cyanide-free methods for lysing erythrocytes and measuring Hb have been developed. U.S. Pat. No. 5,250,437 (to Toda et al.) and U.S. Pat. No. 5,242,832 (to Sakata) all utilize quaternary ammonium salt lysis systems for hemolyzing erythrocytes and oxidizing the hemoglobin. However, because of the harshness of the quaternary ammonium ion based systems on leukocytes, these systems cannot be used for combined leukocyte subpopulation differentiation greater than three subpopulations and Hb determination, particularly if near native state, leukocyte differentiation is desired.

EPO No. 0 325 710 (to Hamaguchi et al.) uses a polyethylene based nonionic surfactant for the hemolysis of red blood cells. However, the system presented by Hamaguchi et al. has limited capabilities for analysis of leukocyte subpopulations, and in a single measurement can only differentiate three subpopulations in addition to measuring the hemoglobin.

SUMMARY OF THE INVENTION

An ideal lysis reagent system would selectively and rapidly lyse red blood cells, while leaving leukocytes in such a state so as to allow for the automated analysis of near native state lymphocytes, monocytes, eosinophils, basophils and neutrophils as distinct subpopulations of cells. Further, this reagent system would be appropriate for use with human and non-human animal samples and for analysis of either normal or pathological blood samples.

One object of the present invention is to provide a lysis reagent which overcomes some or all of the disadvantages of the prior art discussed herein.

Another object of the present invention is to provide compositions having the ability to selectively lyse red blood cells and enable the determination of five distinct leukocyte populations in whole blood samples within a single analysis step.

Another object of the present invention is to provide cellular lysis compositions for red blood cell lysis.

The lytic reagent composition of the present invention contains a long chain ethoxylated amine compound represented by the formula:

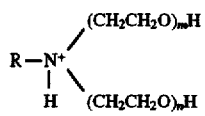

wherein R is an alkyl, alkenyl or alkynyl group having 12–22 carbon atoms, m and n are each 1 or more, m+n is between 20 and 40 and acid to adjust the pH of the reagent to be within the range of 2.0 to 3.6.

Another object of the present invention is to use the present lytic reagent composition in a lytic reagent system for the lysis of red blood cells and, in the same assay, allow for the determination at least three, preferably at least four and most preferably at least five distinct leukocyte populations in a single step measurement. The lytic reagent system utilizes the lytic reagent composition having concentrations of an ethoxylated long chain amine compound and acid sufficient to selectively hemolyze red blood cells in a whole blood sample, while leaving the leukocytes intact and creating modifications in the leukocytes to enable their automated differentiation. The lytic reagent system includes a hypertonic alkaline stabilizing reagent which is added subsequent to red blood cell lysis to inhibit further lytic activity and prevent swelling of leukocytes, retaining the leukocytes in their near physiological state. This lytic reagent system has the additional advantage of functioning entirely at room temperature, 18° to 28° C.

An additional object of the present invention is to provide an automated method of differentiating at least three, preferably at least four and most preferably at least five distinct leukocyte subpopulations, subsequent to red blood cell lysis. This method entails mixing a blood sample with the lytic reagent composition described above for a brief period of time, less than 10 seconds, followed by addition of the hypertonic alkaline stabilizing reagent. Cells are analyzed using a hematology analyzer capable of D.C. volume (D.C.), RF size (RF), opacity, light scatter and fluorescence measurements.

A further object of the present invention is to provide for diagnostic methods of determining the presence of pathologies resulting in altered populations of leukocyte subpopulations.

Another object of the present invention is to provide a lysis reagent system which is compatible with non-human animal samples.

Another object of the present invention is to provide a lytic reagent system which can be used reproducibly on blood samples which are many hours old.

Another object of the present invention is to provide a lytic reagent system which is effectively insensitive enough to the sample lipid content, to permit its use for the differential analysis of bone marrow and other non-peripheral fluid samples.

Another object of the present invention is to provide a lysis reagent system which preserves cell surface morphology and permits cellular analysis based on fluorescent labelling and immunohistochemistry of cell surface markers in addition to analysis based on DC, Rf and light scatter measurements.

An additional object of the present invention is to provide a lysis reagent system which can be used for simultaneous measurement of hemoglobin (Hb) and leukocyte determination in a blood sample.

DETAILED DESCRIPTION OF THE INVENTION

1) The Lytic Reagent Composition

Figure 1:
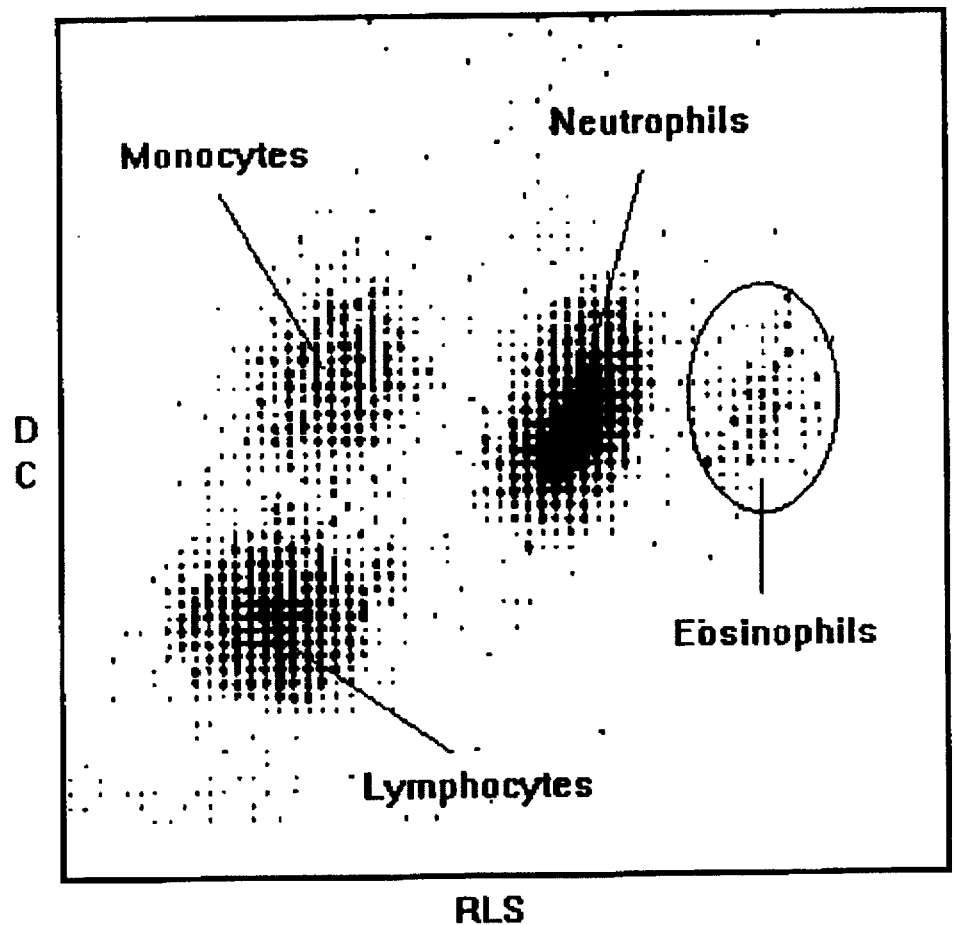
FIGS. 1–10 and 15–16 are scattergrams of results obtained in accordance with the practice of the present invention as described in Examples III, IV, V and VI.

In one embodiment, the present invention is directed to lytic reagent composition comprising an ethoxylated long chain amine compound and an acid to adjust the pH of the composition.

The ethoxylated long chain amine compound of the present invention has a lipophilic tail and a branched hydrophilic, polar head group and can be represented by the formula:

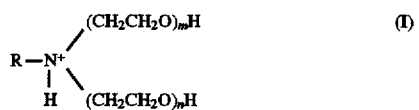

wherein R is an alkyl, alkenyl or alkynyl having 12 to 22 carbon atoms; m and n are each 1 or more, and m+n is 20 to 40. In the above structure, R is preferably 14 to 20 carbon atoms and m and n can be the same or different numbers.

The ethoxylated long chain amine compound of the formula (I) can be synthesized by procedures known in the art as described, for example, in Porter, M. R., Handbook of Surfactants, Chapman & Hall, NY, pp. 147–150 (1991). When synthesized by the known procedure, m and n in the above formula should have approximately equal values. However, m and n need not have the same values.

It has been found that the hydrophile and the lipophile balance plays a role in the lytic potency of the cationic ethoxylated long chain amine compounds used in the lytic reagent composition of the present invention. In general, the lytic potency increases as the size of the hydrophilic polyoxyethylene head group decreases and decreases as the head group size increases.

When the total polyoxyethylene units exceed 40, the lytic reagent composition becomes too weak and cannot lyse the red blood cells using the preferred conditions disclosed herein. An ethoxylated long chain amine compound containing less than 20 oxyethylene units is too lytic, which causes damage to the leukocytes. This damage will prevent the obtaining of five subpopulations of leukocytes. By having an appropriate hydrophile/lipophile balance, the lytic reagent composition is able to selectively lyse the red blood cells without damaging the leukocytes during the differential measurement.

The concentration of the ethoxylated long chain amine compound in the lytic reagent composition needs to be in an amount sufficient to selectively hemolyze the red blood cells in a whole blood sample, while leaving the remaining leukocytes essentially intact. The concentration of the ethoxylated long chain amine compound in the lytic reagent composition has been found to be effective in a broad range from about 8 g/L to about 80 g/L, preferably 12 g/L to 50 g/L.

The function of the acid in the lytic reagent composition is two-fold. First, it assists in red blood cell lysis by creating an acidic medium in the blood and lytic reagent mixture. Under the conditions of the present invention, the lytic reaction can take less than ten (10) seconds and preferably less than seven (7) seconds to sufficiently lyse the red blood cells and break the red cell ghosts and debris down to a level that will not interfere with the leukocyte detections and differentials. This selective and fast lytic activity preserves the leukocytes in near native conditions by avoiding prolonged exposure to the lytic reagent. For the purposes of this disclosure, near native condition means that cellular morphology is preserved so that analysis of the cellular subpopulations can be performed using histochemical or fluorescent labelling of cell surface markers.

The second function of the acid is to create only slight modifications to the leukocytes to allow appropriate separations among leukocyte subpopulations in a DC versus light scatter scattergram and a DC versus RF scattergrams.

The acid is used in an amount sufficient to adjust the pH of the lytic reagent composition in the range of approximately 2.0 to 3.6. The acid will usually be an effective amount of an organic acid. Preferably, formic acid or an effective mixture of formic acid with another organic acid or an inorganic acid is used. The organic acid to be used in admixture with the formic acid can be, for example, acetic, citric, oxalic, glycolic or propionic acid or a mixture of two or more of the aforementioned acids. Inorganic acids which can be mixed with the formic acid include, but are not limited to, hydrochloric, sulfuric and phosphoric acid.

Optionally, one or more solubilizers can be included in the lytic reagent composition in an amount effective to improve the efficiency of the lysing process. Typically, the solubilizers are polyoxyethylene and polyoxypropylene copolymers. Suitable solubilizers include but are not limited to Pluronic copolymers manufactured by BASF Corporation, Parsippany, N.J., such as Pluronic F38 and Pluronic 25R8.

Additional optional additives can also be included in the lytic reagent composition in concentrations that their presence is compatible with the primary functional components of the lytic reagent composition. Among these additives are preservatives which have anti-oxidant properties, to increase the shelf-life of the composition, and which have anti-microbial properties. Preservatives which have anti-oxidant properties include but are not limited to EDTA and butylmethylphenol. Preservatives which have anti-microbial activity include but are not limited to dimethyloldimethyl hydantoin, iodopropynylbutyl carbamate and isothiozolone derivatives.

The ethoxylated long chain amine compound is used to create a cationic compound in an acidic environment. It is believed that because of their cationic nature, the ethoxylated long chain amines can absorb more efficiently onto negatively charged red cell membrane than nonionic or anionic polyoxyethylene based surfactants and more efficiently promote the hemolysis. This intrinsic difference between the cationic ethoxylated long chain amines and the nonionic ethoxylated alcohols, phenols and esters may be the reason that the former, used in the present invention, provides superior hemolysis of whole blood samples.

However, the mechanism by which the lytic reagent composition reacts with both red and white cell fractions, and the ability to distinguish one fraction from the other is not entirely clear.

2) The Stabilizing Reagent Composition

The present invention is also directed to a lytic reagent system comprising the lytic reagent composition and a hypertonic, alkaline stabilizing reagent.

The stabilizing reagent composition is added subsequent to red blood cell lysis to inhibit further lytic activity. More specifically, the function of the stabilizing reagent composition is to neutralize the acid in the blood mixture and prevent swelling of leukocytes so that the leukocytes are preserved for the purposes of automated analysis, including differentiation.

The stabilizing reagent composition is an aqueous buffered salt solution comprised of a simple physiological salt or salts. The salt or salts used in the stabilizing reagent composition can be a mixture of chloride salts and sulfate salts. The chloride salt can be, but is not limited to, sodium chloride or potassium chloride in a concentration of about 0.25 to 4% based on the total weight of the stabilizing reagent composition. The sulfate salt can be, but is not limited to, sodium sulfate or potassium sulfate in a concentration of about 0.25 to 9% based on the total weight of the stabilizing reagent composition. The stabilizing reagent composition is hypertonic and can have an osmolality of about 950 to 1800 mOsm. The salt concentration which affects the osmolality of the stabilizing reagent composition can vary because the volume of the stabilizing reagent composition can be adjusted relative to the lytic reagent volume so that the final osmolality of the blood sample mixture is between approximately 400 to 600 mOsm.

The buffer may be any physiological buffer including, but not limited to, potassium or sodium carbonate, potassium or sodium phosphate, Tris, and potassium or sodium tetraborate. The pH of the stabilizing reagent composition is an approximate pH of 7 to 12.5, preferably having a pH of 9 to 11.5.

3) Description of Complete Lysis Reagent System for Specific RBC Lysis and Leukocyte Differentiation The present invention is also directed to a lytic reagent system comprising a lytic reagent composition to lyse red blood cells and a hypertonic, alkaline stabilizing reagent composition to be added to the blood sample subsequent to red blood cell lysis in an automated differential analysis of leukocytes.

The lytic reagent system can be used in an analysis of the treated whole blood and enables the differentiation of at least two subpopulations of leukocytes. Preferably at least three subpopulations and more preferably at least four subpopulations and most preferably at least five subpopulations are differentiated which include neutrophils, lymphocytes, monocytes, eosinophils and basophils.

The stabilizing reagent composition provides a hypertonic medium after being mixed with the blood sample mixture which contain the blood sample and lytic reagent composition so that the final osmolality of the test sample is from about 400 to 600 mOsm, preferably 410 to 520 mOsm.

For the blood sample mixture, to achieve the best separation among the leukocyte subpopulations, a slight hypertonic condition is preferred, instead of a physiologically isotonic environment. The hypertonic environment created by the stabilizing reagent composition by its high physiological salt content prevents the swelling of the leukocytes that would result from their exposure to the lytic reagent composition and prevents the cell damages due to such swelling. In fact, a slight cell shrinkage occurs upon interaction with the stabilizing reagent for a few seconds, which produces a more confined cell distribution among the leukocyte subpopulations.

Unlike traditional acid lysing systems or some lysis reagent systems based on nonionic polyoxyethylene surfactants, a hypotonic environment is not required by the current invention for the lysing of red blood cells and the lytic reagent composition can lyse the red blood cells even under isotonic conditions. In the preferred embodiment of the lytic reagent system, the lytic reagent is slightly hypotonic, approximately 100 mOsm to 250 mOsm. The addition of the stabilizing reagent composition converts the test sample to a slightly hypertonic environment which does not produce a dramatic osmotic stress to the leukocytes. The use of the lytic reagent system results in a much tighter distribution within each subpopulation and a superior population separation when compared to the performances of prior art reagents and methods.

The generation of at least 4, preferably at least 5, distinct subpopulations of cells allows for the analysis of these subpopulations in a one step analysis system based on the differences in the combined RF, DC and light scatter profiles of the cells and circumvents the need to perform differential lysis of the leukocytes for full determination of the individual subpopulations, particularly the individual granulocyte subpopulations. Previous lysis reagent systems permitted only two parameter analyses in a given analysis step. Thus, to fully obtain a profile of five leukocyte subpopulations, a complex method of three individual determinations followed by a combined analysis of the determinations was required.

Moreover, because the lytic reagent system of the present invention preserves cellular morphology, further analysis of the cellular subpopulations can be performed using histochemical and fluorescent labelling of the leukocyte cell with cell surface markers. For example, labelling of cell surface antigens allow for further differentiation of the lymphocyte population into CD4 and CD8 cells.

The leukocytes of aged and abnormal blood samples are usually fragile or sensitive to the lysing reagents and are difficult to analyze by automated blood analyzers. The harshness of most lysis reagent systems, particularly acid based lysis systems, precludes their use for analysis of any but fresh blood samples, as the cells become too fragile as they age.

The advantage of this system for preventing leukocyte damage allows this reagent system to be used not only for differential analysis of freshly collected blood samples, but also for analysis of blood samples several hours after sample collection and abnormal blood samples. The lack of harsh osmotic and acid shocks in the present invention allow for analysis of blood which is several hours old. More specifically, the present invention can be used with blood samples several hours (6 or more hours) old.

The lytic reagent system of the present invention provides an additional advantage of operating entirely at room temperatures, 18° to 28° C. Lysis reagent systems previously operated at an elevated temperature, 30° C. or higher, for adequate separation of eosinophils and basophils. This elevated temperature requirement necessitated analysis instrumentation which was significantly more complex, as the reactions must be thermostatically controlled. The present invention overcomes this need for thermostatic control by operating optimally at room temperature.

Another advantageous feature of this invention is that the lytic reagent system is less sensitive to the lipid contents of the whole blood samples, which improves the accuracy of the automated differential analysis for the high lipid blood samples, and eliminates the sample pre-dilution which is typically required to compensate for the lipid content in the plasma.

In addition, because of the lytic reagent composition being insensitive to the lipid contents of blood samples, the lytic reagent system of this invention can be used for the differential analysis of non-human animal blood samples which can have different lipid contents. This allows for the first time a convenient method of performing leukocyte analysis of at least four subpopulations, preferably five subpopulations, in a veterinary environment.

Still further, because the lytic reagent composition is insensitive to the lipid content, the lytic reagent system can be used in the differential analysis of other fluid samples which may have dramatically different lipid contents, such as bone marrow.

The lytic reagent system can be sold as a kit wherein the lysis reagent composition is packaged in a container, such as a plastic container, and the hypertonic alkaline stabilizing reagent composition is packaged in a separate container, such as a plastic container. The two containers can be packaged together in a third container, such as a box. Instructions on how to use the reagents in accordance with the present invention are preferably included inside or on or associated with the third container, or either or both of the two reagent containers.

4) Method for Stromatolysis of Red Blood Cells and Automated Differentiation and Analysis of Leukocyte Subpopulations Changes in specific subpopulations of leukocytes can be indicative of particular disease states. One of the hallmarks of the transition from HIV infection to full blown AIDS is a marked decrease in the level of lymphocytes, Fauci et al., Ann. Intr. Med., 114, 678 (1991). Abnormal levels and morphologies of lymphocytes can also be seen with leukemias. Increased levels of both monocytes and lymphocytes are identified with acute inflammation and have been associated with diseases such as tuberculosis, granulomatous and leprosy, Gallin et al. in Inflammation: Basic Principles and Clinical Correlations, (1992). Many autoimmune conditions including autoimmune hemolytic anemia and lupus show increased levels of neutrophils, Malech and Gallin, N. Engl. J. Med., 317, 687 (1987). Also, many parasitic infections, particularly those caused by helminth parasites, are associated with eosinophilia, Noble et al. in Parasitology, The Biology of Animal Parasites (1989). The present invention will be useful for the analytical and diagnostic procedures involved in identifying changes in one or more leukocyte subpopulations which may accompany any of, but not limited to, the above mentioned pathologies.

A blood sample can be obtained from a patient by conventional phlebotomy techniques. Typically used anticoagulant agents, including heparin, EDTA, acid citrate dextrose (ACD) and sodium citrate do not affect the performance of the present invention.

Subsequent to gathering, the blood sample is briefly mixed with the lytic reagent composition as described above.

The amount of time of exposing the blood sample to the lytic reagent composition prior to addition of the stabilizing reagent composition is important for the differentiation method for leukocyte subpopulations presented by this invention. This exposure period should preferably not exceed ten seconds, and is preferably less than seven seconds. These exposure times are specified for ambient temperature (18° to 28° C.). Increasing the temperature at which the lysis is performed correspondingly decreases the exposure time. Likewise, decreasing the temperature increases the exposure time. After the brief exposure to the lytic reagent composition, an appropriate amount of the stabilizing reagent composition is added and the cells are analyzed within about 15 seconds after addition of the stabilizing reagent composition.

The leukocyte fraction of the whole blood sample, treated in the above procedure, can be readily differentiated into at least two subpopulations of leukocytes. Preferably at least three subpopulations and more preferably at least four subpopulations and most preferably at least five subpopulations are differentiated, which include neutrophils, lymphocytes, monocytes, eosinophils and basophils.

Four subpopulations, and more preferably five subpopulations, of leukocytes can be differentiated after exposure of a blood sample to the current lytic reagent system using a single step measurement system utilizing combined DC, RF and light scatter based on the subpopulations' respective abilities to cause a shift in the impedance of an electric field, such a shift being proportional to the cell volume; abilities to impede a radio frequency (RF) current and abilities to scatter light. For the purposes of this disclosure, a single step measurement means that a single aliquot of blood can be used with the same lytic reagent composition of this invention to obtain a differentiation of the lymphocyte subpopulation with at least one other subpopulation of leukocytes consisting of eosinophils, basophils and neutrophils. Preferably, this differentiation is measured in less than 30 seconds and more preferably less than 20 seconds after the addition of the lytic reagent composition.

The detection methods used for the differentiation of leukocytes by a hematology analyzer are generally described in U.S. Pat. No. 5,125,737, to Rodriguez et al., which is hereby incorporated by reference in its entirety.

An ethoxylated long chain amine compound is used to create a cationic compound in an acidic environment. It is believed that because of their cationic nature, the ethoxylated long chain amines can absorb more efficiently onto negatively charged red cell membranes than nonionic or anionic polyoxyethylene based surfactants and more efficiently promote the hemolysis. This intrinsic difference between the cationic ethoxylated long chain amines and the nonionic ethoxylated alcohols, phenols and esters may be the reason that the former, used in the present invention, provides superior hemolysis of whole blood samples.

Previous lysis reagent systems permitted only two parameter analyses in a given analysis step. Thus, to fully obtain a profile of five leukocyte subpopulations, a complex method of three individual determinations on the same sample followed by a combined analysis of the determinations was required.

Figure 2:
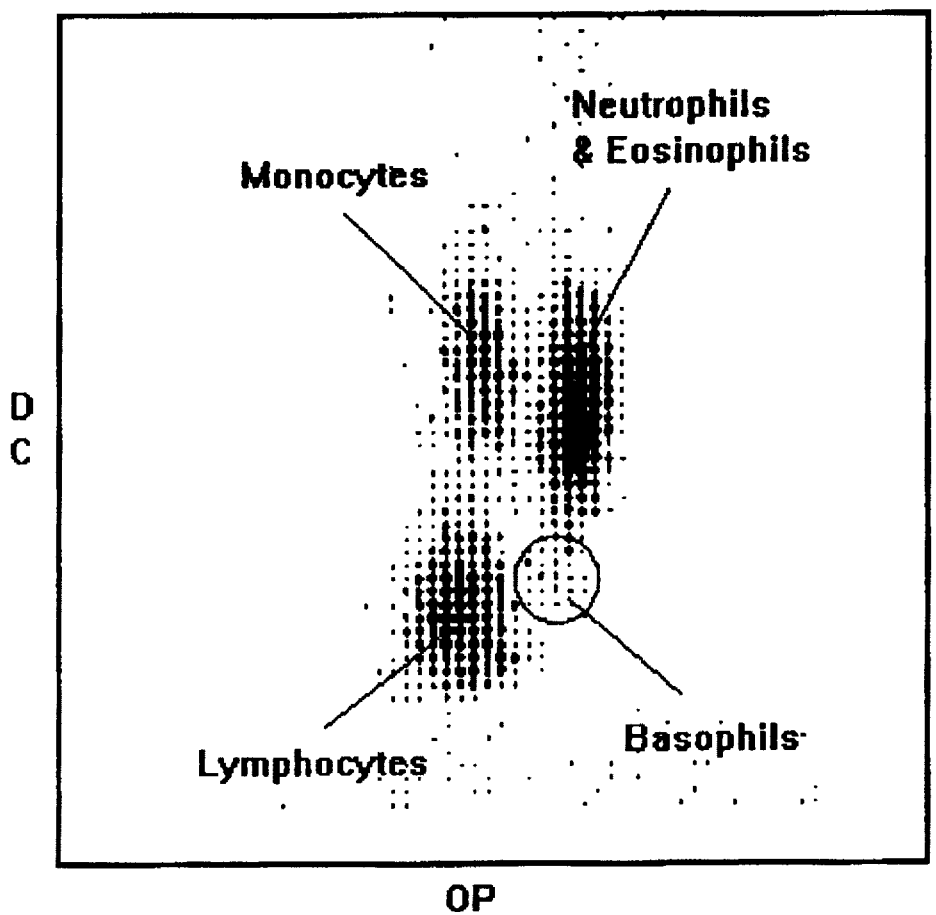

Although the present method has been described in detailed terms using an analysis being conducted with combined DC, RF and LS measurements, it is within the contemplation of this invention to use the lytic reagent system in a mode of analysis selected from the group consisting of DC, RF, LS, opacity (OP) and combinations thereof. The results of such mode of analysis can be seen from the figures wherein DC versus RF is shown in FIG. 2; and DC versus LS is shown in FIG. 1. As appreciated by one skilled in the art, the mode of analysis can be only DC, which would result in at least two populations of leukocytes.

5) Method for Hemoglobin Determination

More than 300 abnormal hemoglobins have been discovered upon examination of patients with clinical symptoms and by electrophoretic surveys of a clinically normal population. Many of these abnormalities result in clinical pathologies having altered hemoglobin levels or Hb having an altered ability to bind oxygen. Among these diseases are sickle cell anemia, both α- and β-thalassemias and hemoglobin M, Stamatoyannopoulos G. et al. (Eds), Molecular Basis of Blood Disorders (1986).

An ability to measure hemoglobin in blood samples is an essential part of diagnostic analysis and is also important for monitoring responsiveness to therapies directed towards diseases which affect Hb and to therapies which are directed towards other diseases but which may have adverse side effects on the Hb level. Ideally, one would like to be able to accomplish multiple diagnostic analyses in a single automated step. The present invention allows for the analysis of at least three, preferably four, and more preferably, five subpopulations of leukocytes in conjunction with a determination of the Hb.

Lysis of erythrocytes with the lytic reagent composition causes the release of Hb as oxyhemoglobin. Addition of the stabilizing reagent composition results in the formation of a stable chromogen which has a maximum absorbance peak at 540 nm and a shoulder at 570 nm. This system provides several advantages over the methods of Hb measurement of the prior art. Unlike the previous methods, the present invention allows for the differentiation and analysis of leukocyte subpopulations in their near native state along with a determination of the Hb. In addition, the stabilizing reagent composition converts the oxyhemoglobin to the chromogen in less than 10 seconds, allowing for rapid automated analysis, and the chromogen once formed is stable for up to 20 minutes.

EXAMPLE I

Lytic Reagent Composition a) A lytic reagent composition encompassing the ethoxylated long chain amine compound of structure I has been formulated with the following composition:

A cationic ethoxylated long chain amine compound with formula:

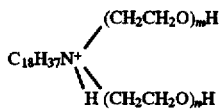

where m+n has a value of 30, was dissolved in deionized water at a concentration of 20 g/L. Formic acid was used to adjust the pH to 3.2. In addition, the following preservatives were added: 0.2 g/L EDTA, 0.5 g/L Proclin 300 (Rohm & Haas Co.), and 0.05 g/L 2,6-Di-tert-butyl-4-methylphenol.

b) A lytic reagent composition encompassing the ethoxylated long chain amine compound of structure I has been formulated with the following composition:

A cationic ethoxylated long chain amine compound with formula:

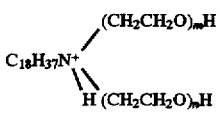

where m+n has a value of 25, was dissolved in deionized water at a concentration of 18 g/L. 10 g/L Pluronic 25R8 (BASF) was added as a solubilizer and 1.6 ml/L Formic acid was used to adjust the pH to 3.2.

c) A lytic reagent composition encompassing the ethoxylated long chain amine compound of structure I has been formulated with the following composition:

A cationic ethoxylated long chain amine compound with formula:

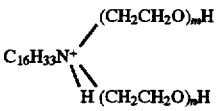

where m+n has a value of 30, was dissolved in deionized water at a concentration of 20 g/L. 5 g/L of Pluronic F38 (BASF) was added as a solubilizer and 1.6 ml/L of formic acid was used to adjust the pH to 3.2. In addition, the following preservatives were added: 0.2 g/L EDTA, 0.5 g/L Proclin 300 (Rohm & Haas Co.), and 0.05 g/L 2,6-Di-tert-butyl-4-methylphenol.

EXAMPLE II

Lytic Stabilizing Reagent a) Carbonate Buffer Based Stabilizing Reagent

A stabilizing reagent has been formulated as described above and is comprised of 14 g/L of NaCl, 32 g/L of $Na_2SO_4$, and 6.6 g/L of $Na_2CO_3$ buffer, pH adjusted to 11.0. The osmolality of this reagent is about 1080 mOsm.

b) Phosphate Buffer Based Stabilizing Reagent

A stabilizing reagent has been formulated as described above and contains 8.3 g/L $Na_2HPO_4$, 12.2 g/L $Na_3PO_4$, 14.3 g/L NaCl and 31 g/L $Na_2SO_4$, pH adjusted to 11. The osmolality of this reagent is about 1190 mOsm.

EXAMPLE III

Lysis of RBC and Differentiation of Normal Human Leukocyte Populations

The lytic reagent system of this invention was prepared in deionized water from reagent grade chemicals and ethoxylated long chain amine compounds of industrial purity.

a) 20 g of the cationic ethoxylated long chain amine compound described in Example I a) was dissolved in 1 L of water. The pH of the ethoxylated long chain amine compound solution was adjusted to 3.2 by formic acid. 0.2 g of EDTA and 0.5 g of Proclin 300 (Rohm and Haas Co.) were added as antioxidant and anti-microbial preservatives, respectively. To 31 μl of a whole blood sample, 560 μl of the lytic reagent composition was added and the mixture was gently mixed by swirling for 4 seconds at room temperature (approximately 21° C.).

Figure 3:
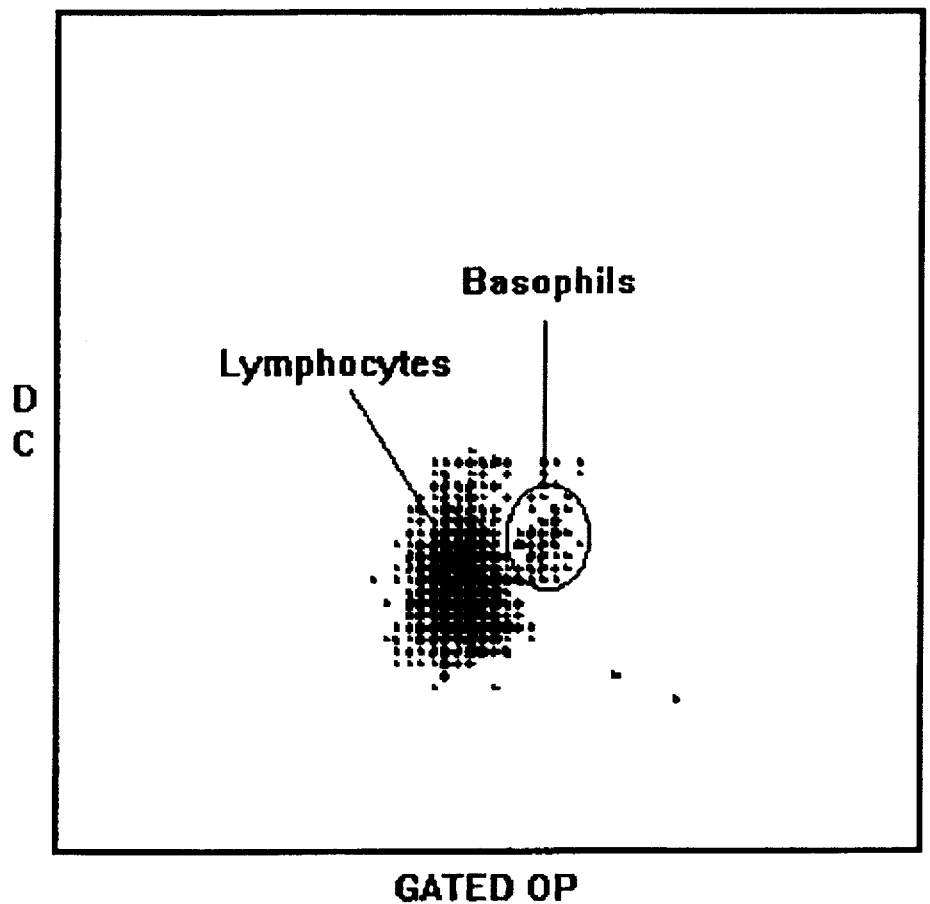

The lysing reaction was retarded by the addition 230 μl of an aqueous stabilizing reagent composition containing 14 g/L of NaCl, 32 g/L of $Na_2SO_4$ and 6.6 g/L of $Na_2CO_3$, pH 11.0. The blood mixture was gently mixed and ready for differential analysis 15 seconds after the addition of the stabilizing reagent. The final blood mixture was kept at neutral pH (about 7) and in hypertonic condition with a osmolality about 445 mOsm. Three-dimensional differential analysis was conducted on a COULTER® STKS hematology analyzer with DC, RF and light scatter measurements utilizing a focus flow technique and ISOTON® III as a sheath fluid. The resulting scattergrams are illustrated in FIG. 1 and FIG. 2. Four distinct subpopulations of leukocytes were identified and quantified in the DC vs. rotated light scatter (RLS) scattergram, FIG. 1. FIG. 2 illustrates the separated leukocyte subpopulations in the scattergram of DC vs. Opacity (a function of RF and DC). A fifth subpopulation of the leukocyte, basophils, is isolated by gating out other overlapping subpopulations in the DC vs. opacity scattergram. The isolated basophil population is depicted in the scattergram illustrated in FIG. 3.

Figure 14:
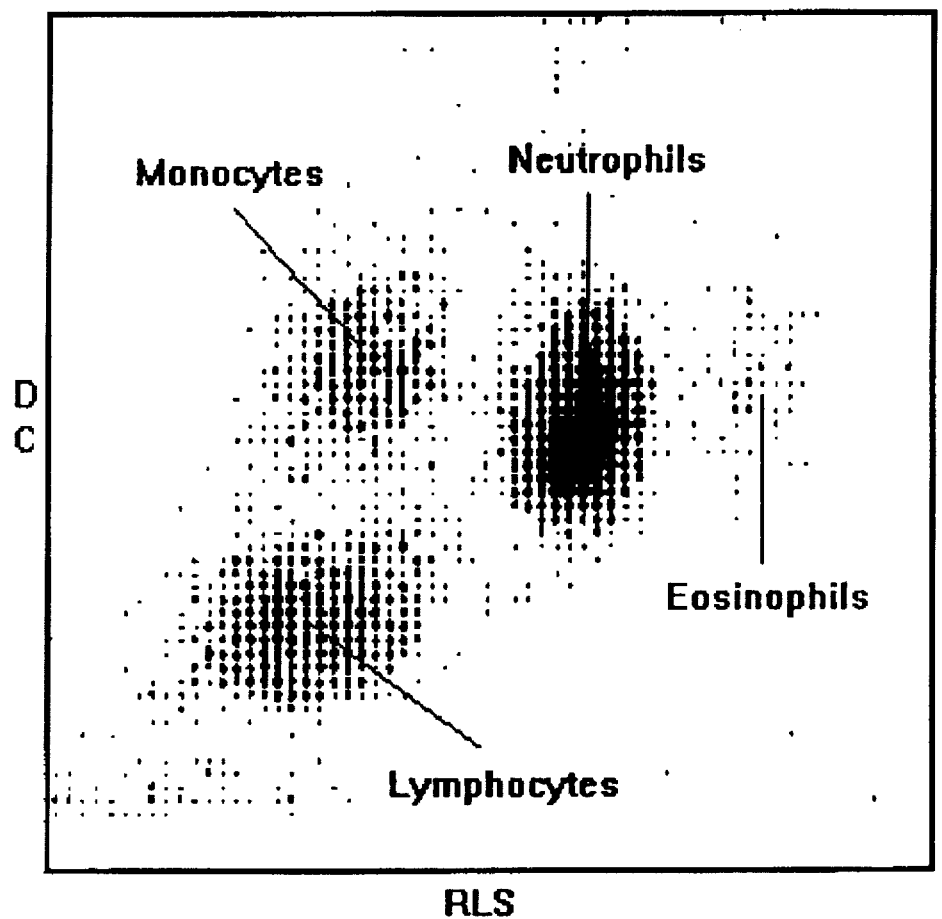
Figure 15:
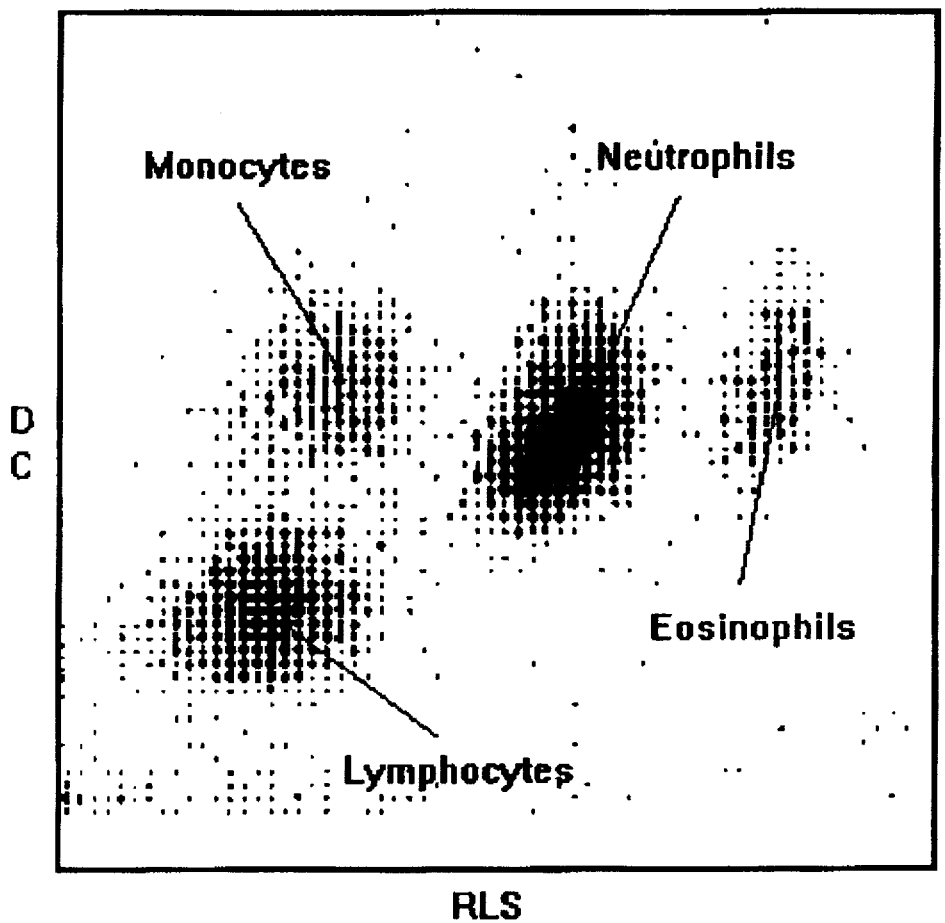
Figure 16:
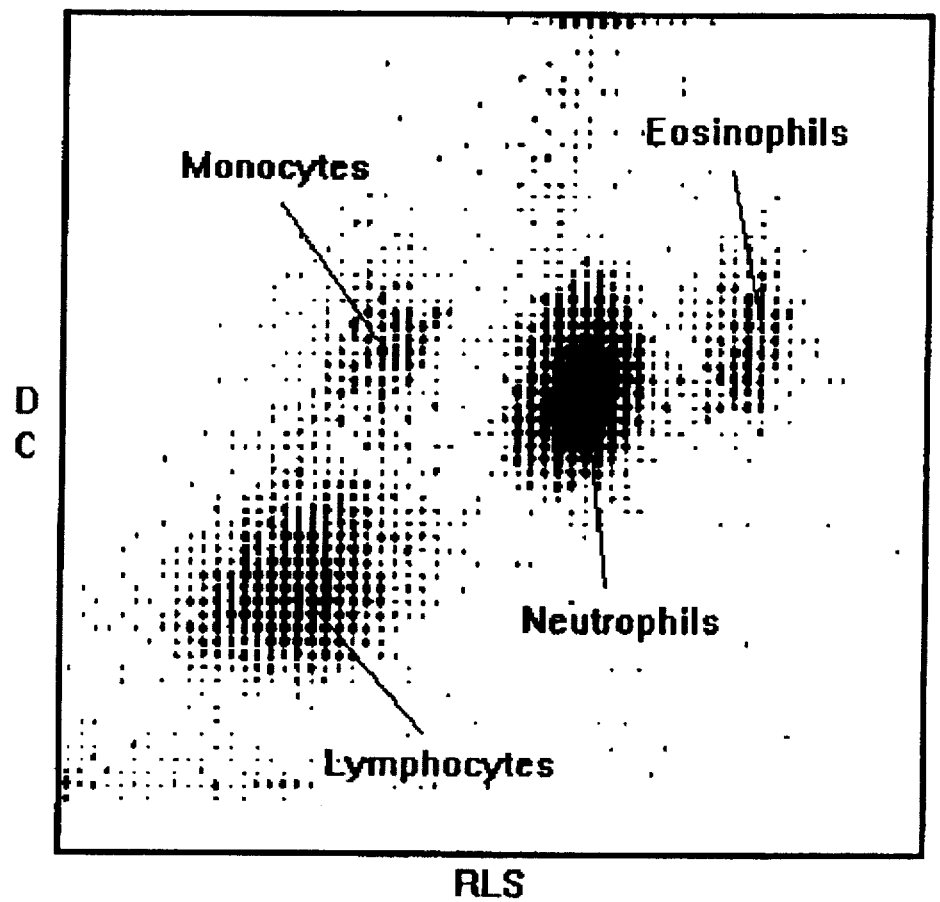

Alternatively, by using a phosphate buffered stabilizing reagent as in Example II to inhibit the lysis reaction and stabilize the leukocytes, good differentiation of the leukocyte subpopulations is obtained. FIG. 14 shows four of the leukocyte subpopulations, including lymphocytes, monocytes, neutrophils and eosinophils.

b) Using the procedure described above with the lytic reagent composition of Example I b), selective lysis of the red blood cells and differential analysis of leukocyte subpopulations was performed. FIG. 15 shows four leukocyte subpopulations seen with the DC vs. light scatter scattergram obtained from this analysis. A fifth leukocyte subpopulation, basophils, can be obtained by gating the acquired data as described above.

c) Using the procedure described above with the lytic reagent composition of Example I c), selective lysis of the red blood cells and differential analysis of leukocytes subpopulations was performed. FIG. 16 shows the DC vs. light scatter scattergram obtained from this analysis. This scattergram distinctly shows four of the leukocyte subpopulations including lymphocytes, monocytes, neutrophils and eosinophils. The basophils can be obtained by gating the acquired data as described above.

EXAMPLE IV

Figure 4:
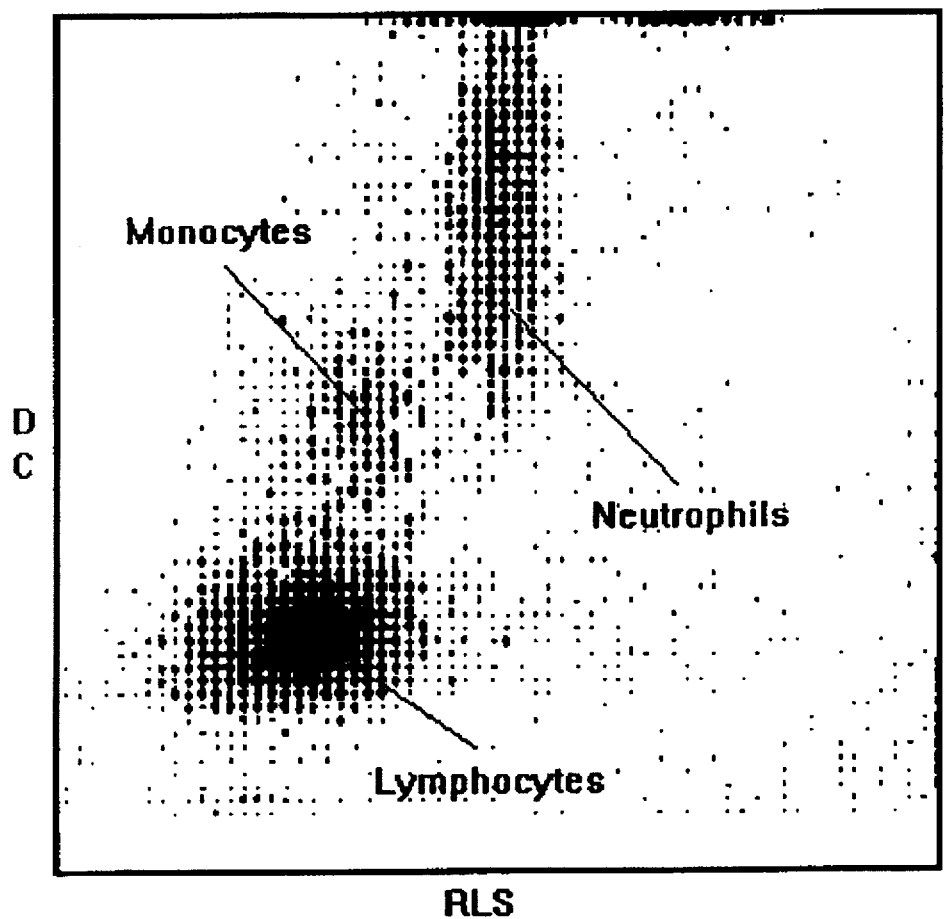
Figure 12:
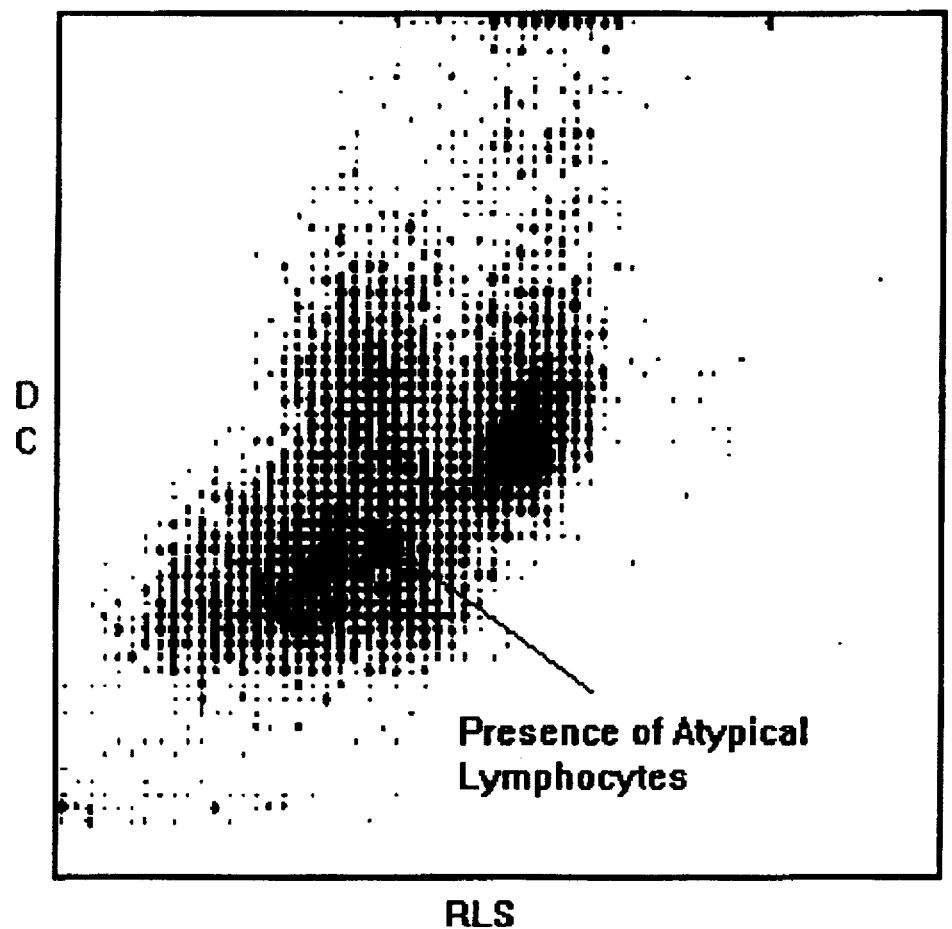
FIGS. 12–14 are scattergrams of results obtained in accordance with the practice of the present invention as described in Examples III and IV.
Figure 13:
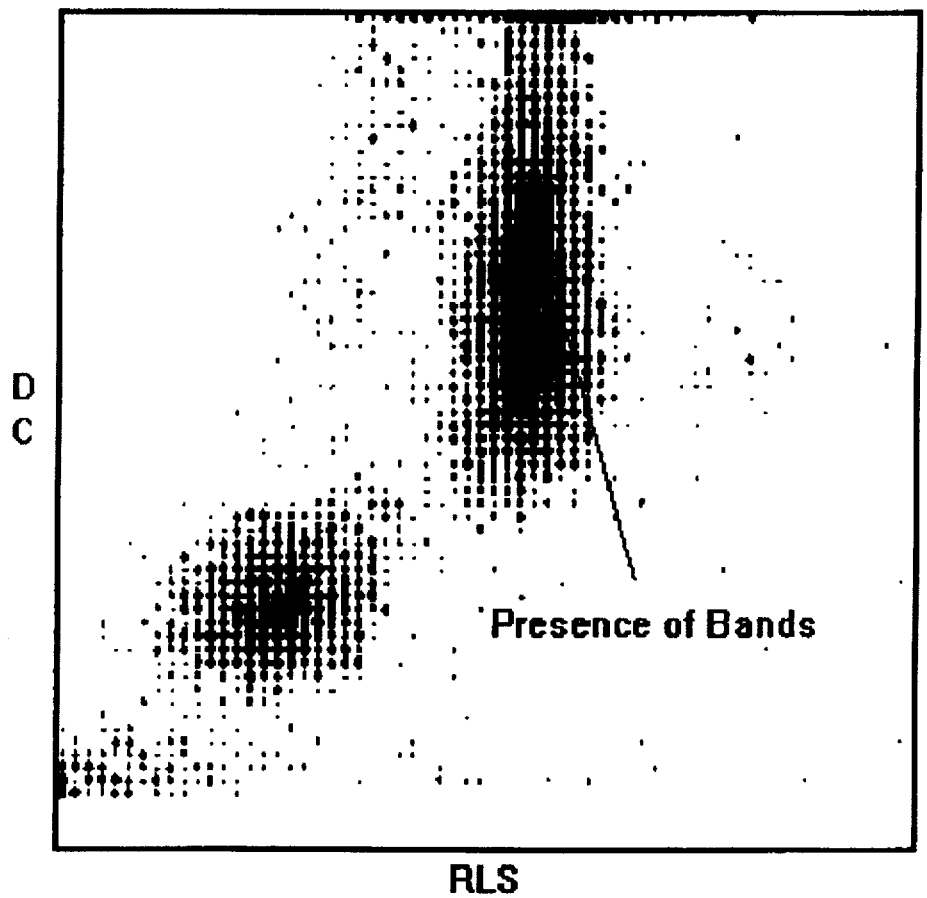

Lysis RBC and Differentiation of Abnormal Human Leukocyte Populations a) The procedure of Example III was repeated for leukocyte differentiation of blood from an active sickle cell patient, using the same reagents as in Example III. It has been commonly seen that active sickle cell blood is difficult to lyse by some commercial hypotonic acid lysing reagents and the subsequent population separation among the leukocyte subpopulations is poor. In these cases, a false differential report can be generated by an automated hematology analyzer. As shown in FIG. 4, a clear population separation indicating the presence of pathology by the abnormality leukocyte differentials, was obtained for the active sickle cell blood sample by using the reagent system of this invention, demonstrating that this invention can also be used for abnormal blood analysis.

b) The procedure of Example III was repeated for leukocyte differentiation of blood from a patient having acute lymphocytic leukemia. As seen in FIG. 12, analysis of the blood sample using the lysis reagent system and automated hematology analysis indicates the presence of atypical lymphocytes.

c) Using the procedure and reagents of Example III, the presence of bands, indicative of immature granulocytes in a blood sample of a patient diagnosed with breast cancer, was shown (FIG. 13) to be preserved.

EXAMPLE V

Lysis RBC and Differentiation of Non-Human Animal Leukocyte Populations

Figure 5:
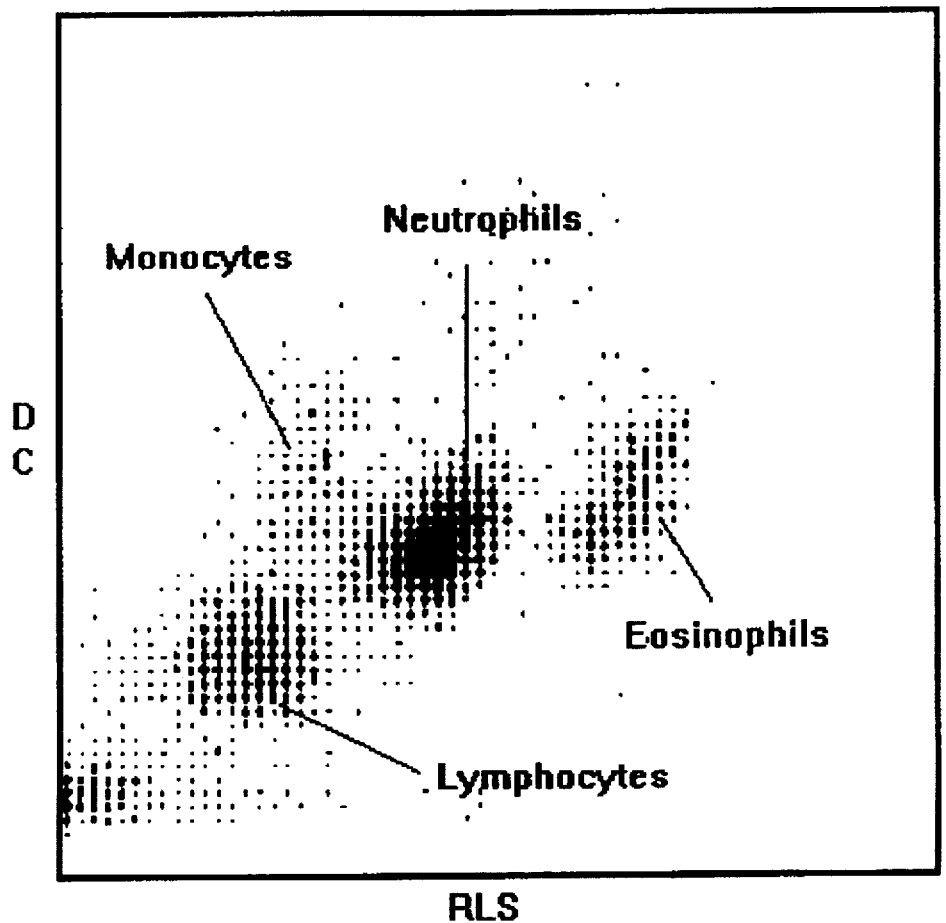
Figure 6:
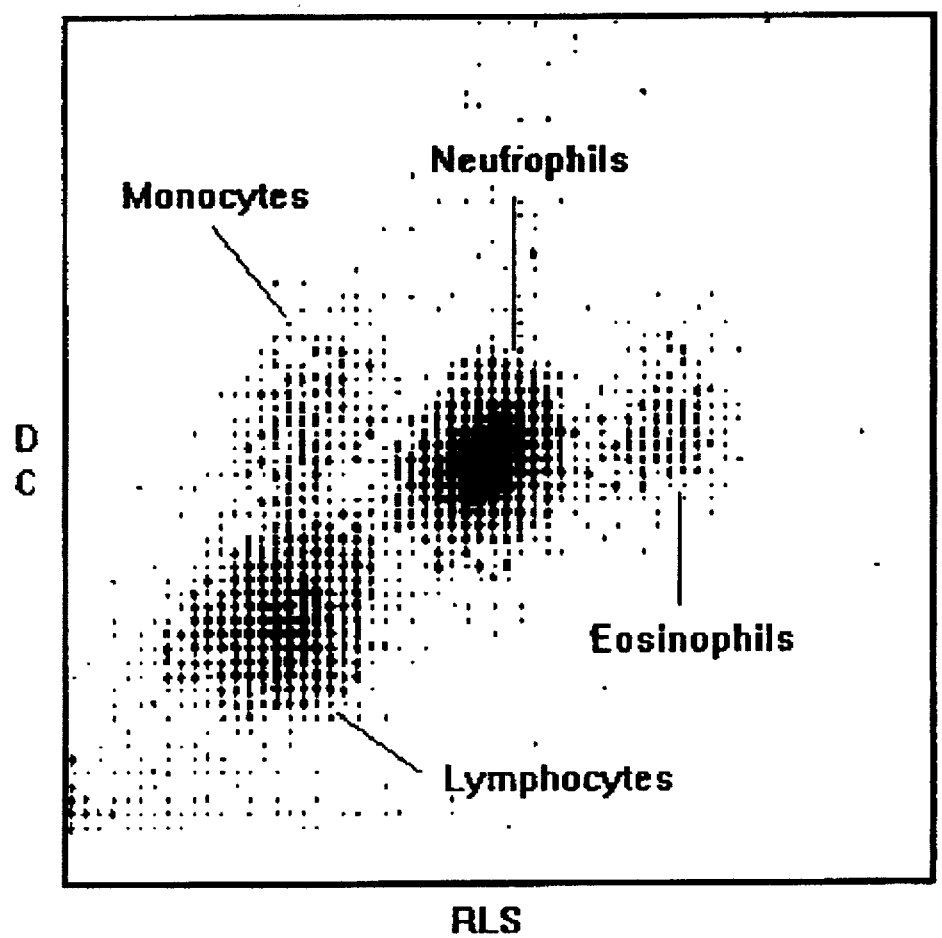
Figure 7:
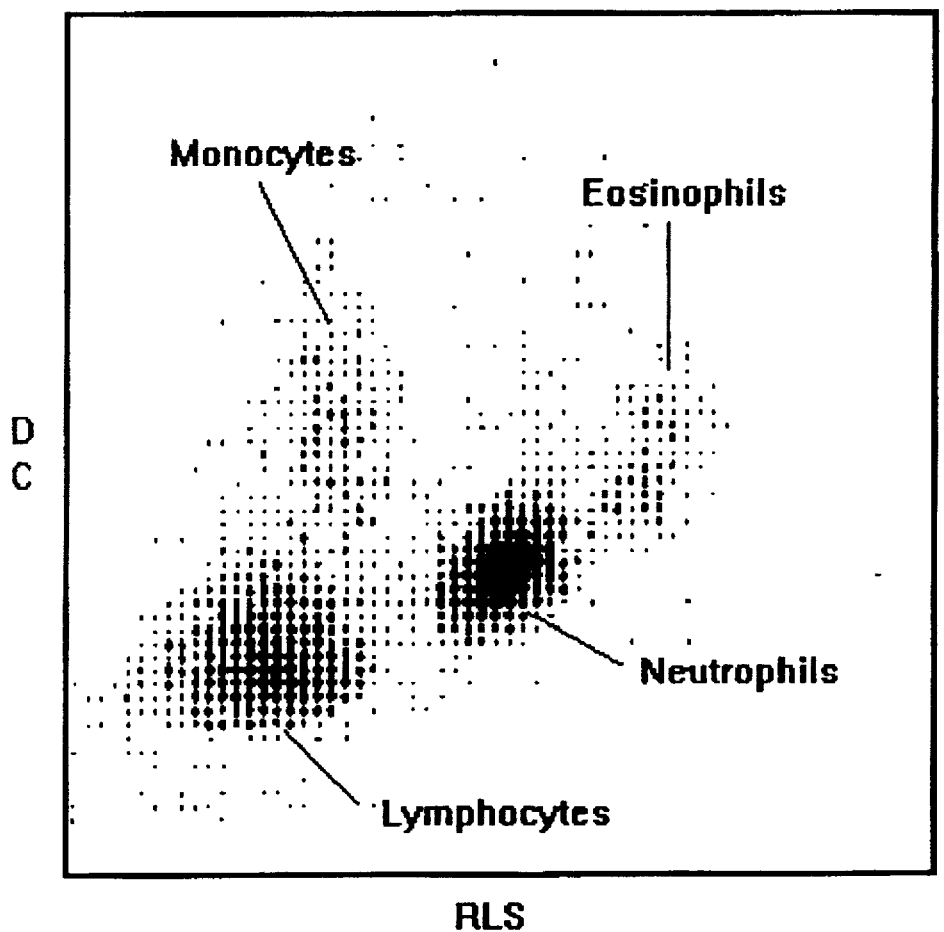
Figure 8:
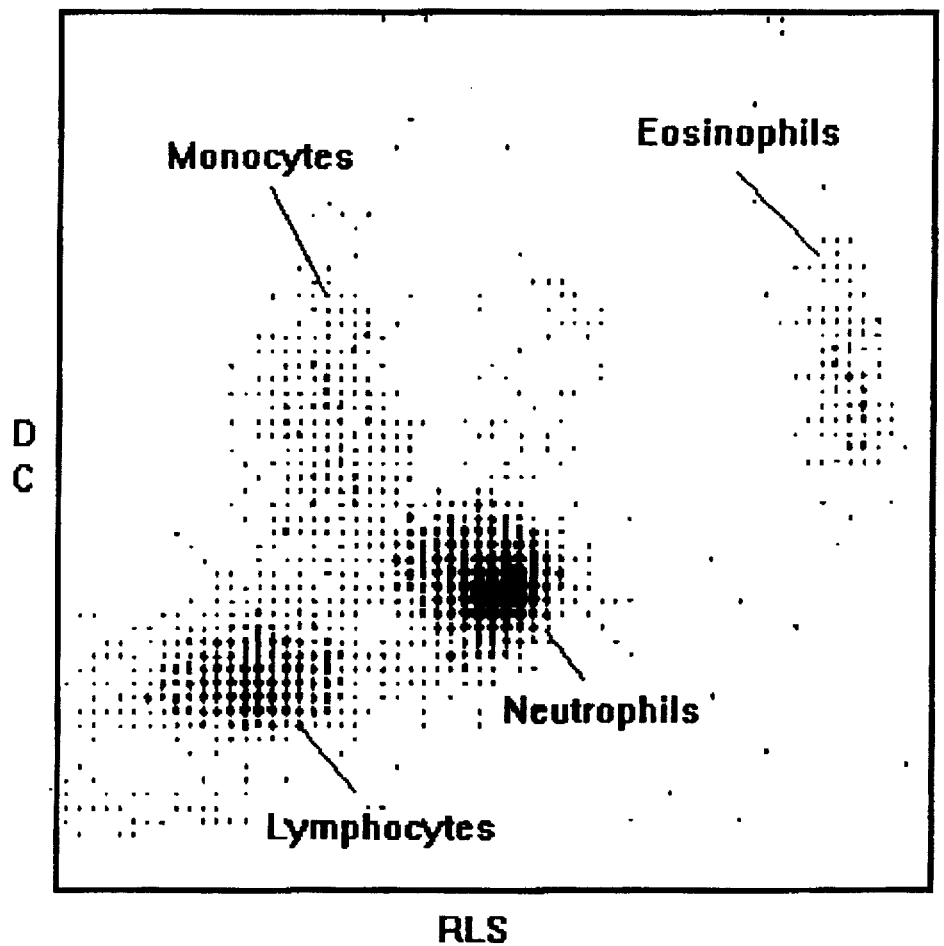
Figure 9:
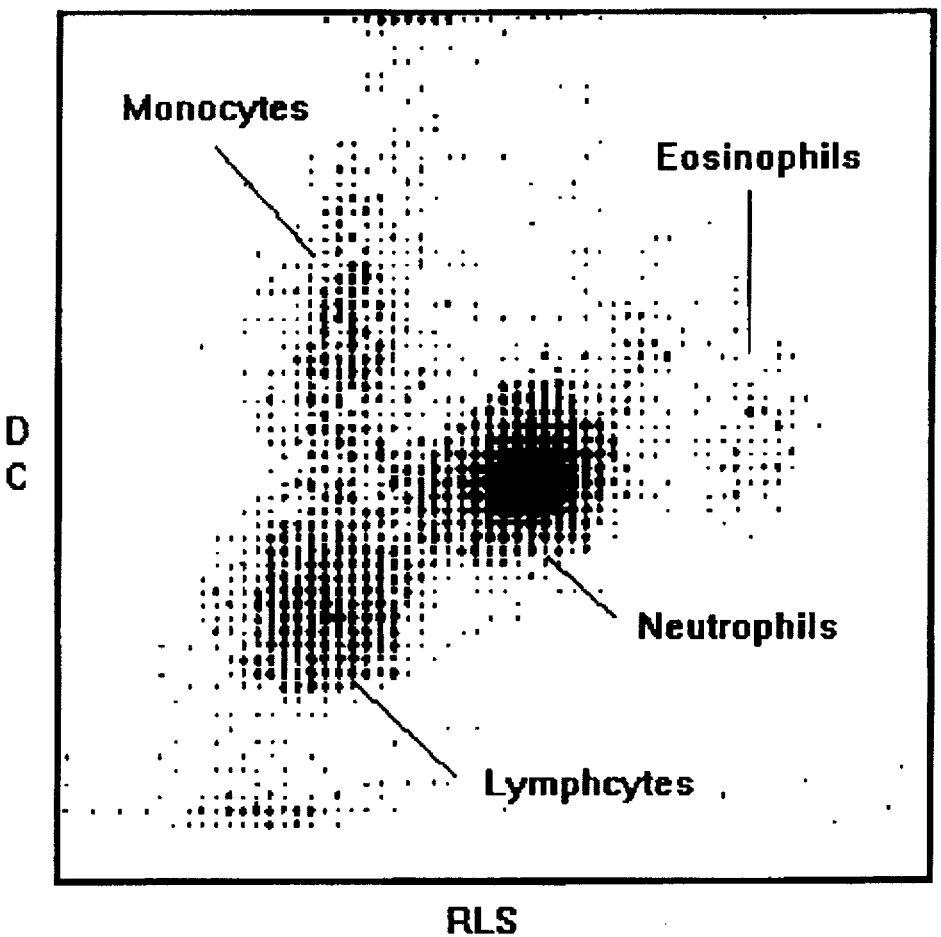

Several veterinary whole blood samples were analyzed using the same lytic reagent composition and stabilizing reagent composition and the method described in Example III, except that the lytic reaction time varied among the different species from 2 to 7 seconds and the stabilizing reagent composition interaction time was from 6 to 20 seconds. The lytic reaction times and stabilizing reagent interaction times are consistent between different experiments performed on a given species. The resulting DC vs. light scatter scattergrams are shown in FIGS. 5 to 9 with following order: FIG. 5, canine whole blood sample; FIG. 6, simian whole blood sample; FIG. 7, caprine whole blood sample; FIG. 8, equine whole blood sample and FIG. 9, guinea pig whole blood sample.

As shown by the scattergrams, although each species has its own characteristics in terms of the respective subpopulation distribution, the leukocyte subpopulations including lymphocytes, monocytes, neutrophils and eosinophils within a species, are clearly distinct from each other. Among different species, the lytic reaction time and reagent volume can be varied in order to obtain the best differential results, but such variations can be easily accomplished by automated blood analyzers.

This invention allows, for the first time, an ability to differentiate at least four different subpopulations of leukocytes, i.e., lymphocytes, monocytes, neutrophils and eosinophils, with veterinary whole blood samples utilizing an automated method.

EXAMPLE VI

Figure 10A:
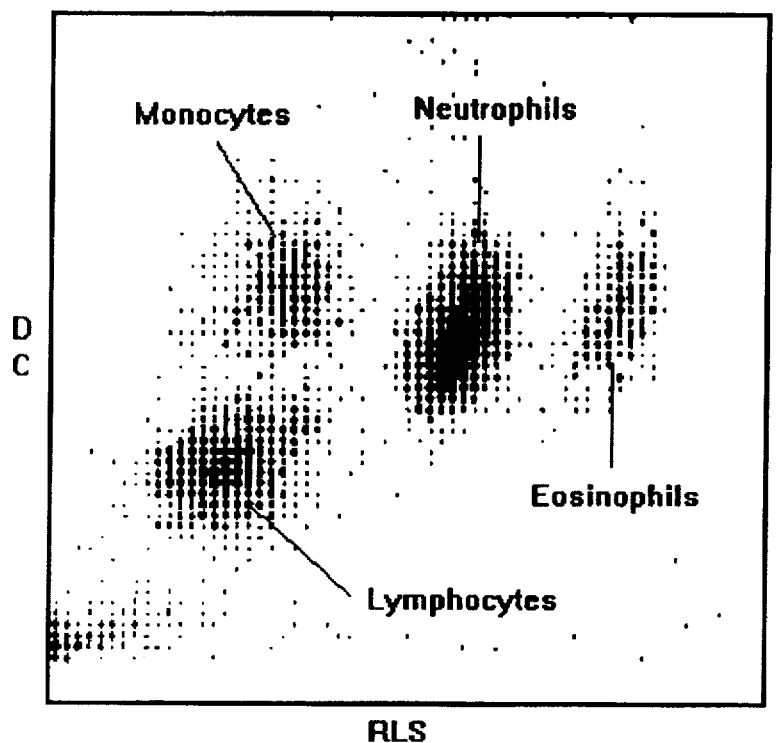
Figure 10B:
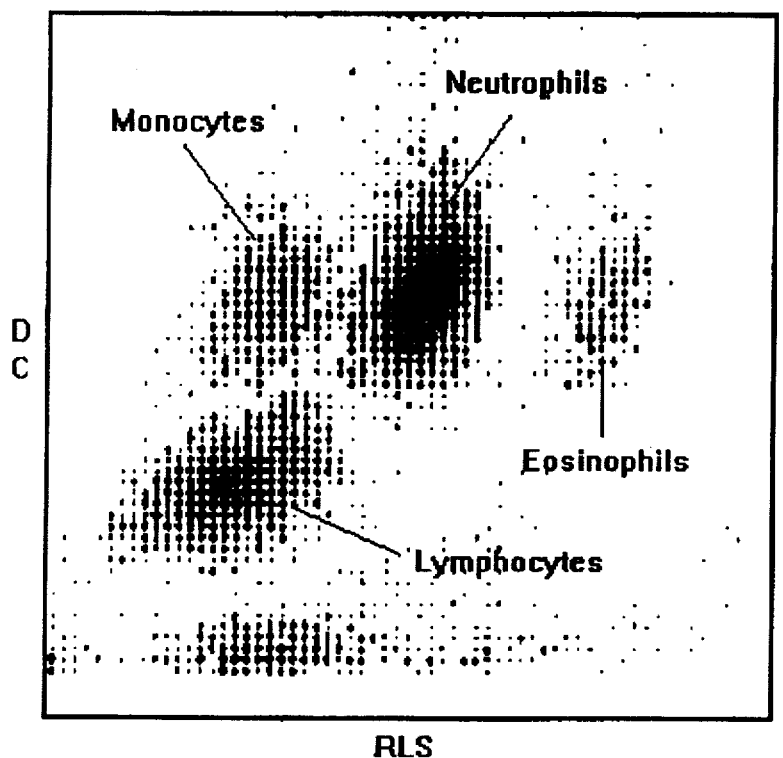

Lysis RBC and Differentiation of Human Leukocyte Populations From Aged Blood Samples The procedure of Example III was repeated utilizing the same lytic and stabilizing reagents for leukocyte differentials of a whole blood sample several hours after gathering for direct comparison of the differentiation with fresh blood samples. The sample was stored at room temperature, approximately 21° C. As clearly shown in FIG. 10, similar leukocyte subpopulation profiles were obtained for fresh blood, FIG. 10A, and blood samples that were 27 hours old, FIG. 10B, demonstrating that this invention can be used for leukocyte differentiation and analysis several hours after blood sample collection. The extended whole blood life for automated leukocyte differential is a result of the stabilization effects on leukocytes with the reagent system of this invention.

EXAMPLE VII

Hb Determination of Normal Blood Samples

Figure 11:
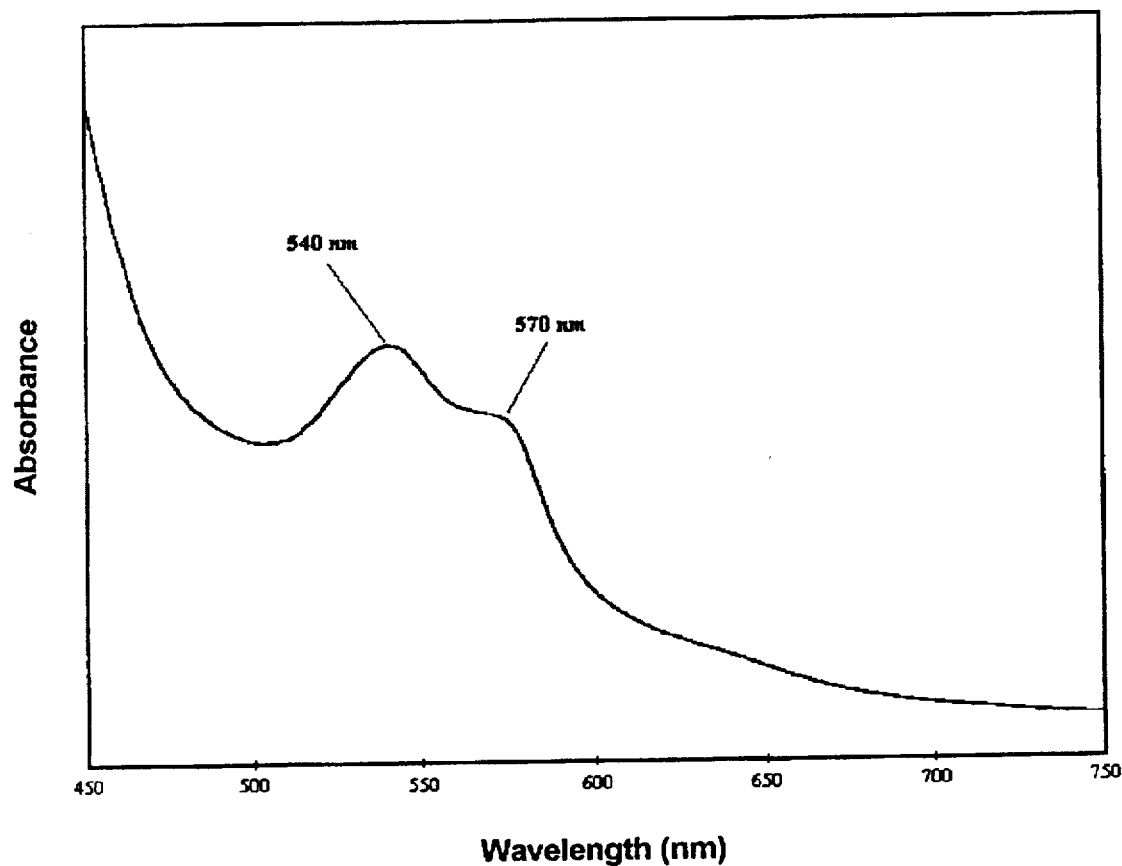
FIG. 11 is a graph illustrating the absorption profile of the sample described in Example VII.

The lytic reagent system of Example III was used in the determination of Hb in whole blood samples. 14 µl of whole blood were mixed with 1224 µl of the lytic reagent composition and gently mixed for 5 to 8 seconds. 498 µl of the stabilizing reagent composition was added and after 10 seconds, an absorption profile of the resulting chromogen was measured. As seen in FIG. 11, the chromogen has a maximum absorption peak at 540 nm with a shoulder at 570 nm. The chromogen formed less than 10 seconds after addition of the stabilizing reagent and was stable for more than 20 minutes.

EXAMPLE VIII

Whole Blood Leukocyte Differentials by Fluorescence

The lytic reagent system of Example III has been used in conjunction with fluorescent labelling of cell surface markers. A blood sample is stained with an aqueous dye solution at a 10:1 ratio for a few minutes. 28 µL of the stained blood sample is aspirated to a hematology analyzer with the same reagent volumes and reaction times to the regular 5-part differential analysis described in Example III. The sample mixture is analyzed by fluorescence and DC. The major populations, i.e., lymphocytes, monocytes, neutrophils and eosinophils, can be clearly separated. This not only demonstrates the preservation of cell surface morphology with the lysis reagent system, but also allows for further diagnostic capabilities based on alterations of cell surface markers on any one of the five subpopulations of leukocytes which can be differentially identified.

EXAMPLE IX

Selective Lysis and Differential Analysis of Non-Blood Fluid Sample

To 14 µL of a non-peripheral fluid sample, bone marrow, approximately 1200 µL of the lytic reagent composition of Example I will be added and the mixture will be gently mixed by swirling, either manually or automatically, for about 2 to 7 seconds at room temperature (approximately 21° C.). The lysing reaction will be retarded by the addition of about 490 µL of the stabilizing reagent composition of Example II. The sample mixture will be gently mixed for a few seconds and ready for differential analysis 7 to 18 seconds after the addition of the stabilizing reagent composition. The differential analysis will be conducted on a hematology analyzer described in Example III. The leukocyte subpopulations will be identified and quantified using the scattergrams illustrated in Example III.

What is claimed is:

1. A lytic reagent composition comprising:

(a) an ethoxylated long chain amine compound represented by the general formula:

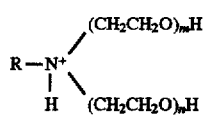

wherein R is an alkyl, alkenyl or alkynyl group having 12 to 22 carbon atoms, m and n are each 1 or more and m+n is between 20 and 40;

(b) acid to adjust the pH of the lytic reagent composition to be within the range of 2.0 to 3.6; and (c) a preservative;

wherein said lytic reagent composition is in an amount effective for cell analysis.

2. The lytic reagent composition of claim 1, wherein R is an alkyl group having 14 to 20 carbon atoms.

3. The lytic reagent composition of claim 1, wherein said compound in the lytic reagent composition is at a concentration of 8 g/L to 80 g/L.

4. The lytic reagent composition of claim 1, wherein the acid used to adjust the pH comprises an organic acid.

5. The lytic reagent composition of claim 4, wherein the acid used to adjust the pH comprises an effective mixture of formic acid and an acid selected from the group consisting of acetic, citric, oxalic, glycolic, propionic, hydrochloric, sulfuric and phosphoric and mixtures thereof.

6. A lytic reagent composition comprising:

(a) an ethoxylated long chain amine compound represented by the general formula:

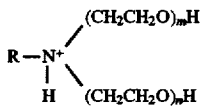

wherein R is an alkyl, alkenyl or alkynyl group having 12 to 22 carbon atoms, m and n are each 1 or more and m+n is between 20 and 40; and (b) formic acid to adjust the pH of the lytic reagent composition to be within the range of 2.0 to 3.6 wherein said lytic reagent composition is in an amount effective for cell analysis.

7. A lytic reagent system comprising:

(a) a lytic reagent composition comprising an ethoxylated long chain amine compound represented by the general formula:

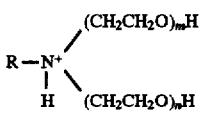

wherein R is an alkyl, alkenyl or alkynyl group having 12 to 22 carbon atoms, m and n are each 1 or more and m+n is between 20 and 40; and an acid to adjust the pH of the lytic reagent to be within the range of 2.0 to 3.6, and (b) a hypertonic, alkaline stabilizing reagent composition.

8. The lytic reagent system of claim 7, wherein the hypertonic alkaline stabilizing reagent composition comprises chloride salts, sulfate salts and a buffer.

9. The lytic reagent system of claim 8, wherein the hypertonic alkaline stabilizing reagent composition comprises:

(a) a chloride salt selected from the group consisting of sodium chloride and potassium chloride in an amount of 0.25% to 4% by weight based on the total weight of the stabilizing reagent composition; and (b) a sulfate salt selected from the group consisting of sodium sulfate and potassium sulfate in an amount of 0.25% to 9% by weight based on the total weight of the stabilizing reagent composition.

10. The lytic reagent system of claim 7, wherein the stabilizing reagent composition further comprises a buffer to adjust the pH of said stabilizing reagent composition to a pH of 7 to 12.5.

11. The lytic reagent system of claim 10, wherein the buffer is selected from the group consisting of carbonate, phosphate, Tris and tetraborate.

12. A method for the determination of Hb in a blood sample comprising stromatolysis of red blood cells with a lytic reagent system of claim 7, and measuring light absorbance at about 540 nm.

13. A method for the differential analysis of cellular populations in fluid sample comprising selective hemolysis of subpopulations of cells with a lytic reagent system of claim 7 and analysis of remaining cell populations.

14. The method of claim 13 wherein the fluid sample comprises non peripheral fluid from humans.

15. The method of claim 14 wherein the fluid sample comprises bone marrow.

16. A method for stromatolysis of red blood cells in a blood cell sample comprising exposing a blood sample to a lytic reagent composition for a time sufficient to lyse red blood cells; said lytic reagent comprising an ethoxylated long chain amine compound represented by the general formula:

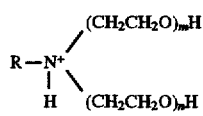

wherein R is an alkyl, alkenyl or alkynyl group having 12 to 22 carbon atoms, m and n are each 1 or more and m+n is between 20 and 40; and an acid to adjust the pH of the lytic reagent composition to be within the range of 2.0 to 3.6.

17. The method of claim 16, which further comprises inhibiting the lysis of leukocytes in the blood cell sample by the addition of a hypertonic, alkaline stabilizing reagent composition.

18. A method for stromatolysis of red blood cells in a blood cell sample and analysis of leukocyte subpopulations comprising:

(a) exposing a blood sample to a lytic reagent composition for a time sufficient to lyse red blood cells, said lytic reagent comprising an ethoxylated long chain amine compound represented by the general formula:

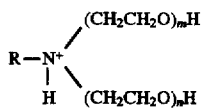

wherein R is an alkyl, alkenyl or alkynyl group having 12 to 22 carbon atoms, m and n are each 1 or more and m+n is between 20 and 40; and an acid to adjust the pH of the lytic reagent composition to be within the range of 2.0 to 3.6; and (b) adding a hypertonic alkaline stabilizing reagent composition to inhibit the lytic action of the lytic reagent composition, and (c) analyzing leukocyte subpopulations contained in the blood cell sample.

19. The method of claim 18 wherein the stabilizing reagent composition stabilizes the leukocytes subpopulations at a pH of 5.0 to 8.5 and in a hypertonic medium of osmolality from 400 to 600 mOsm.

20. The method of claim 19 wherein the stabilizing reagent composition stabilizes the leukocytes subpopulations at a pH of 6.5 to 7.5 and in a hypertonic medium of osmolality from 410 mOsm to 520 mOsm.

21. A method for stromatolysis of red blood cells in a blood cell sample and analysis of leukocyte subpopulations comprising:
   (a) exposing a blood sample to a lytic reagent composition for a time less than 10 seconds, said lytic reagent composition comprising an ethoxylated long chain amine compound represented by the general formula:

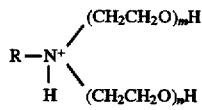

wherein R is an alkyl, alkenyl or alkynyl group having 12 to 22 carbon atoms m and n are each 1 or more and m+n is between 20 and 40; and an acid to adjust the pH of the lytic reagent composition to be within the range of 2.0 to 3.6;
   (b) adding a stabilizing reagent composition to said exposed blood sample, wherein said stabilizing reagent composition inhibits further lytic action and stabilizes leukocytes of a hemolyzed blood sample; and
   (c) differentiating at least two leukocyte subpopulations, consisting of lymphocytes, monocytes, basophils, neutrophils and eosinophils using an automated analyzer.

22. The method of claim 21 wherein the differentiating of at least two leukocyte subpopulations is performed in a single step measurement.

23. The method of claim 21, wherein at least three leukocyte subpopulations are obtained.

24. The method of claim 21, wherein at least four leukocyte subpopulations are obtained.

25. The method of claim 21, wherein at least five leukocyte subpopulations are obtained.

26. The method of claim 21, wherein said blood sample contains an abnormal population of cells.

27. The method of claim 21, wherein the source of the blood sample is a non-human animal.

28. The method of claim 21, wherein the blood sample is older than six hours old.

29. The method of claim 21, wherein said stabilizing reagent composition comprises a hypertonic alkaline solution of chloride salts, sulfate salts and a buffer.

30. The method of claim 29, wherein said hypertonic alkaline stabilizing reagent comprises:

(a) a chloride salt selected from the group consisting of sodium chloride and potassium chloride in an amount of 0.25%–4% by weight based on the total weight of the stabilizing reagent; and (b) a sulfate salt selected from the group consisting of sodium sulfate and potassium sulfate in an amount of 0.25% to 9% by weight based on the total weight of the stabilizing reagent.

31. The method of claim 1, wherein the stabilizing reagent composition further comprises a buffer, wherein the pH of said stabilizing reagent composition is adjusted to a pH of 7 to 12.5.

32. A method for differentiation of at least four subpopulations of leukocytes in a blood sample comprising:
   (a) analyzing a treated blood sample in a single step measurement by an instrument, wherein said single step measurement is performed with a single aliquot of a blood sample with a lytic reagent composition to obtain at least four subpopulations of leukocytes, wherein said lytic reagent comprising an ethoxylated long chain amine compound represented by the general formula:

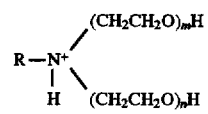

wherein R is an alkyl, alkenyl or alkynyl group having 12 to 22 carbon atoms, m and n are each 1 or more and m+n is between 20 and 40; and an acid to adjust the pH of the lytic reagent composition to be within the range of 2.0 to 3.6; and wherein the mode of analyzing is selected from at least two members of the group consisting of:

(1) D.C. volume,
   (2) RF size,
   (3) opacity,
   (4) light scatter, and
   (5) fluorescence (b) reporting the results of such analysis in an instrument.

33. The method of claim 32 wherein one of the methods of analysis is D.C. volume.

34. The method of claim 32 wherein one of the four subpopulations of leukocytes is basophils.

35. The method of claim 32 wherein one of the four subpopulations of leukocytes is eosinophils.

* * * * *